United States Patent
Sindel et al.

(10) Patent No.: US 7,762,974 B2
(45) Date of Patent: Jul. 27, 2010

(54) ANKLE BRACE WITH MECHANICAL ADVANTAGE CLOSURE SYSTEM

(75) Inventors: Chad M. Sindel, Pleasant Hill, CA (US); Craig J. Koloske, Tracy, CA (US); John M. Petlansky, Tracy, CA (US)

(73) Assignee: Top Shelf Manufacturing, Inc., Tracy, CA (US)

( * ) Notice: Subject to any disclaimer, the term of this patent is extended or adjusted under 35 U.S.C. 154(b) by 438 days.

(21) Appl. No.: 11/511,308

(22) Filed: Aug. 29, 2006

(65) Prior Publication Data

US 2007/0073207 A1 Mar. 29, 2007

Related U.S. Application Data

(60) Provisional application No. 60/712,185, filed on Aug. 30, 2005.

(51) Int. Cl.
*A61F 5/00* (2006.01)
*A61F 5/37* (2006.01)
(52) U.S. Cl. .............................. 602/27; 602/65; 128/882
(58) Field of Classification Search ..................... 602/4, 602/5, 27–29, 65, 19, 20, 23, 60; 128/882
See application file for complete search history.

(56) References Cited

U.S. PATENT DOCUMENTS

| 1,058,322 | A | * | 4/1913 | Mueller ........................ 602/27 |
| 4,863,471 | A | | 9/1989 | Mansat |
| 6,126,625 | A | * | 10/2000 | Lundberg ..................... 602/27 |
| 6,551,264 | B1 | | 4/2003 | Cawley et al. |
| 6,676,620 | B2 | * | 1/2004 | Schwenn et al. .............. 602/12 |
| 7,118,543 | B2 | | 10/2006 | Telles et al. |
| 7,306,571 | B2 | | 12/2007 | Schwenn et al. |
| 2005/0054960 | A1 | * | 3/2005 | Telles et al. .................... 602/19 |
| 2007/0060853 | A1 | | 3/2007 | Sindel et al. |

* cited by examiner

*Primary Examiner*—Patricia M Bianco
*Assistant Examiner*—Keri J Nicholson
(74) *Attorney, Agent, or Firm*—Dickstein Shapiro LLP

(57) ABSTRACT

An orthopedic ankle orthosis having a closure unit with a pull system that provides a mechanical advantage for applying user-desired forces to the ankle joint structures and yet permits the ankle joint to move within a range of motion during activity by the user. The method of using the orthopedic ankle orthosis includes placing the orthosis over a user's ankle, wrapping the lateral and medial body members of the orthosis around the user's ankle, and pulling the elongated pull member to apply user-defined forces to the ankle joint structures.

20 Claims, 2 Drawing Sheets

ANKLE BRACE WITH MECHANICAL ADVANTAGE CLOSURE SYSTEM

This application claims priority to U.S. Provisional Application No. 60/712,185, filed on Aug. 30, 2005, the entire disclosure of which is incorporated by reference herein.

BACKGROUND OF THE INVENTION

1. Field of the Invention

The present invention is directed to a closure system for an ankle brace with an improved pull system to provide a mechanical advantage for applying compression forces to the ankle.

2. Description of the Related Art

Ankle braces are typically removably disposed over one's foot and ankle and fastened in place using a "boot-like" or main body portion which includes a lacing arrangement, a hook and loop fastener (e.g., VELCRO™) type arrangement, or other releasable fastening means. Alternatively, elongate straps may be utilize to surround portions of the foot and ankle area to simulate support similar to that provided by conventional taping procedures that provide a measure of stability and support. Other versions of removable braces include relatively rigid components vertically disposed adjacent to the inner and outer sides of the ankle joint and held in place in the form of splints.

While many of these prior designs provide a degree of support to the ankle joint, there is a need to provide an improved ankle brace which offers greater positive support to the ankle joint structures and yet permits the ankle joint to move within the normal range of motion during activity by the user. There is also a demand for relatively economical ankle braces that can be conveniently used by a patient for a mechanical advantage in exerting compression on the ankle.

SUMMARY OF THE INVENTION

The present invention provides a closure unit for an orthopedic ankle brace that utilizes a closure mechanism comprising two separate pieces working together to create a mechanical advantage ("compression-action") to complete the necessary function of the brace. The mechanical advantage is achieved as the two separate pieces work together through the force enacted from a single pull handle. Preferably, the system may be affixed to a brace formed of soft neoprene, nylon, or foam material, to anatomically fit around the ankle. The ankle brace employing the closure unit of the present invention may be used in the treatment of chronic ankle instabilities and acute ankle injuries such as sprains or strains, for example.

The closure unit is disposed on the lateral side of the brace and includes a first connector member with a first series of channels, and a second connector member with a second series of channels. An elongated flexible pull member is operatively weaved through the respective first and second series of channels to provide a mechanical force advantage when tightened by the patient to draw the first connect member and the second connect member against the patient's ankle to exert compression forces.

The elongated flexible pull member can comprise a cord such as a polyester cord with an exterior braided configuration. The cord is connected at its distal end to a strap handle, which can receive a nap or hook material that can be appropriately positioned, for example, on the lateral side of the ankle brace, so that a patient who pulls the cord to tighten the ankle brace can then secure it at a desired compression.

BRIEF DESCRIPTION OF THE DRAWINGS

Other features and advantages of the present invention will become apparent when the following detailed description is read in conjunction with the accompanying drawings, in which.

DETAILED DESCRIPTION OF THE PREFERRED EMBODIMENT

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein to specifically provide an ankle orthosis with an improved pull system to apply compression forces.

Figure 1:
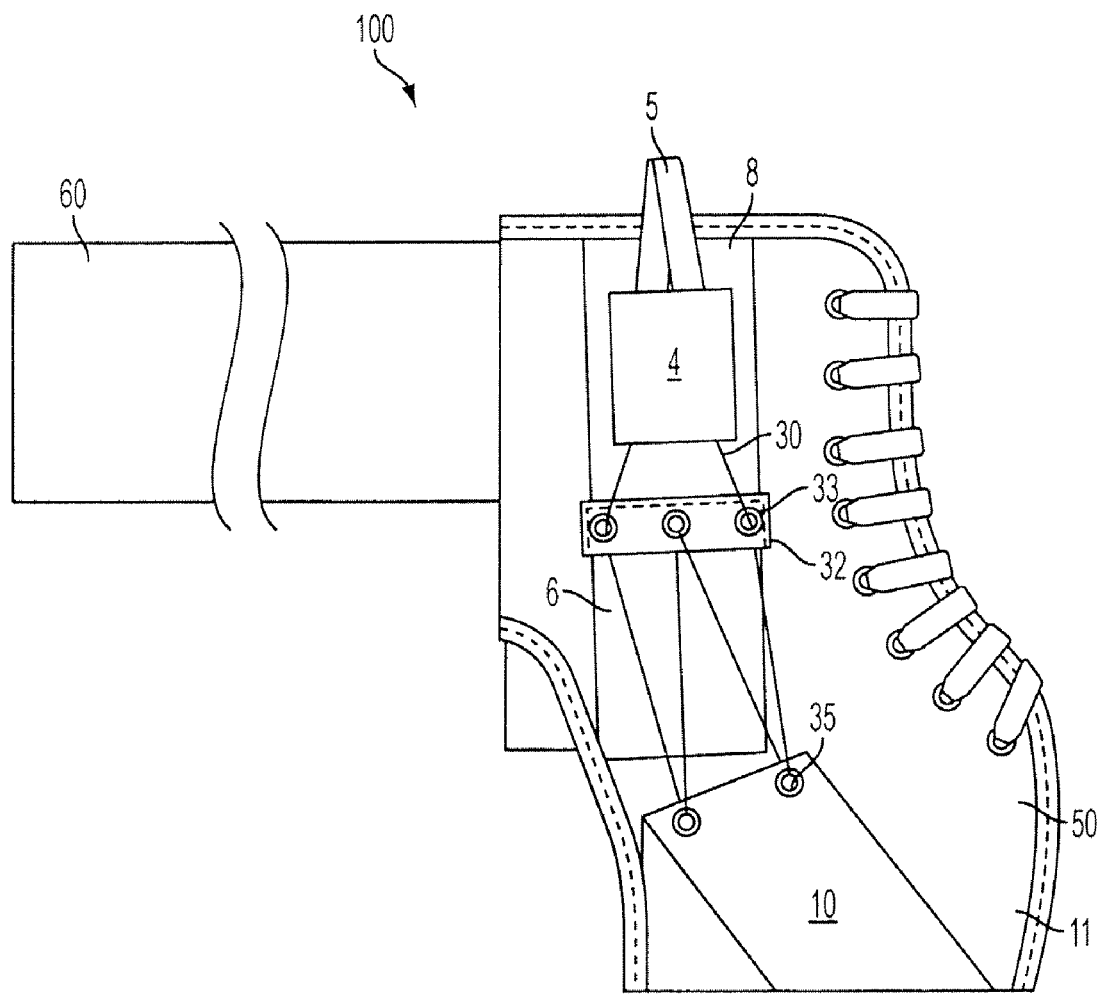
FIG. 1 is a lateral side view of the ankle brace of the present invention.
Figure 2:
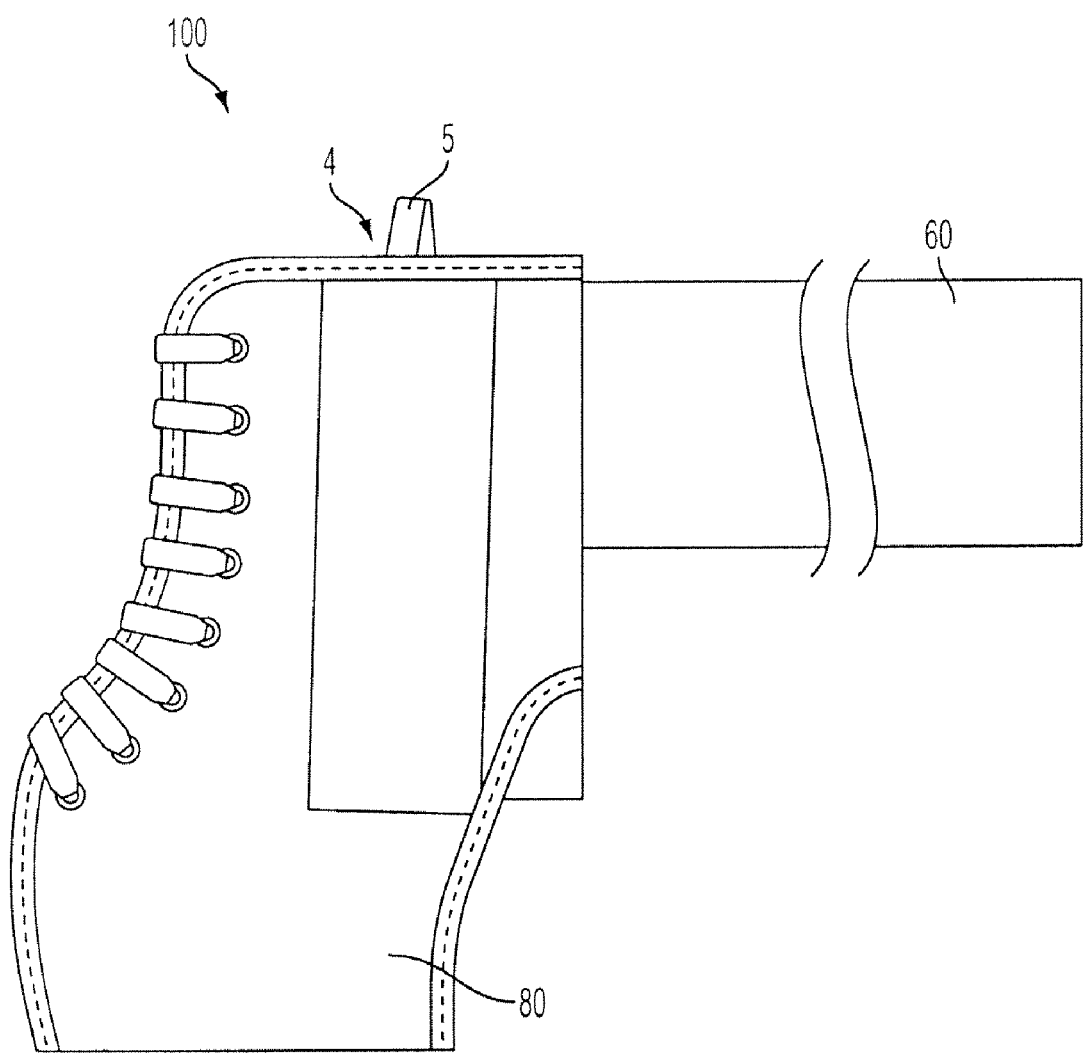
FIG. 2 is a medial side view of the ankle brace of the present invention.

FIGS. 1 and 2 illustrate an exemplary embodiment of ankle brace or orthosis 100 which permits a patient to provide compressive forces about his/her ankle by simply pulling and removably fastening a fastener member 4 to a surface portion of the orthosis.

As can be seen in FIG. 1, a closure unit 6 is provided on lateral side 11 of the orthosis 100. Closure unit 6 includes a first connector member 8 and a second connector member 10. In an exemplary embodiment, the first connector member 8 and the second connector member 10 are provided on lateral body member 50 that conforms to a lateral portion of a patient's ankle. The lateral body member 50 is connected in the front of the foot and ankle with medial body member 80, which conforms to the medial portion of a patient's ankle. The lateral body member 50 is connected with the medial body member 80 using lacing. The lacing connecting the lateral body member 50 and the medial body member 80 may be tightened by pulling the lacing in a conventional manner. The lateral and medial body members 50, 80 may comprise neoprene, nylon or foam material, for example, to anatomically fit around the ankle.

The orthosis may be additionally provided with a separate strap or attaching member 60 having a belt-like configuration, as shown in FIGS. 1 and 2. The attaching member 60 may be, for example, a hook and loop type fastener (e.g., VELCRO™) strap attached to the lateral and medial body members 50, 80 to allow engagement of the orthosis 100 and to further secure the lateral and medial members 50, 80 to the patient's ankle. The strap can be appropriately secured in position by securing the free ends of the straps to the orthosis 100.

Referring to FIG. 1, and in accordance with an exemplary embodiment of the present invention, the closure unit 6 includes a rigid member 32 which is provided as part of the first connector member 8. In a preferred embodiment, the rigid member 32 is provided with a first series of channels 33. The second connector member 10 is provided with a second series of channels 35. The first connector member 8 of the closure unit 6 is attached to a toe-end portion of the orthosis 100. The second connector member 10 of the closure unit 6 is attached to a heel-end portion of the orthosis 100. Although FIG. 1 illustrates a series of three channels 33 on the rigid member 32 of the first connector member 8 and a series of two channels 35 on the second connector member 10, it must be understood that the invention contemplates a closure unit having any number of channels on each of the connector members.

Also illustrated in FIG. 1 is an elongated flexible member or cord 30, which can be formed from a polyester material having an exterior braided surface to thereby provide a low friction, but strong, pull member. The cord member 30 slides within the respective channels 33, 35 in each of the connector members to thereby reduce the friction of a normal brace, while also providing a mechanical advantage or force multiplier when the cord 30 is pulled by the patient.

The cord 30 is connected at its end to the fastener 4, which can have a strap handle 5. The user, by pulling upon the strap handle 5, can then employ a mechanical advantage, via cord 30 and the channels 33, 35, to pull the respective first connector member 8 and second connector member 10 together to provide a compressive force on the ankle. The fastener 4 can then be appropriately secured in position by securing the free end to the orthosis.

The ability of the cord 30 to slide with low friction within the channels 33, 35 provides a relatively compact efficient mechanical advantage without requiring additional moving parts such as pulleys or posts. Thus, a relatively economical and compact adjustable ankle orthosis with an improved closure unit is provided.

The above description and drawings illustrate preferred embodiments which achieve the objects, features and advantages of the present invention. It is not intended that the present invention be limited to the illustrated embodiments, but rather only by the appended claims.

What is claimed as new and desired to be protected by Letters Patent of the United States is:

1. An orthopedic ankle orthosis, comprising:
    a body member configured to cover a patient's ankle; and
    a closure unit, comprising:
        a fastener member, said fastener member being removably attachable to the body member;
        a first connector member having a first series of channels;
        a second connector member having a second series of channels;
        a pull member, said pull member being fixed to the fastener member and operatively weaved through the first series of channels and second series of channels such that by pulling upwardly on said the fastener member the first connector member is tensioned toward the sole of the patient's foot and the second connector member is tensioned toward the first connector member, such that a compression force is applied to the patient's ankle from points above and below the ankle only by the first and second connector members.

2. The orthopedic ankle orthosis of claim 1, further comprising:
    an attaching member attached to said body member and having means to wrap a patient's ankle.

3. The orthopedic ankle orthosis of claim 2, wherein said attaching member comprises a belt-like configuration.

4. The orthopedic ankle orthosis of claim 2, wherein said attaching member comprises a hook and loop fastener.

5. The orthopedic ankle orthosis of claim 1, wherein said body member is made of a material comprising at least one of neoprene, nylon, and foam.

6. The orthopedic ankle orthosis of claim 1, wherein said first connector member of said closure unit is attached to a first portion of said orthosis at or above the patient's ankle.

7. The orthopedic ankle orthosis of claim 1, wherein said second connector member of said closure unit is attached to a second portion of said orthosis at or below the patient's ankle.

8. The orthopedic ankle orthosis of claim 1, wherein said pull member comprises a cord.

9. The orthopedic ankle orthosis of claim 1, wherein said pull member is made of a material comprising polyester and having a braided configuration.

10. The orthopedic ankle orthosis of claim 1, wherein said second connector member is attached to the orthopedic ankle orthosis at a portion configured to cover the sole of a foot.

11. The orthopedic ankle orthosis of claim 1, wherein said first and second connector members can be held in proximity to each other by securing the fastening member to the body member.

12. The orthopedic knee orthosis of claim 1, wherein said fastening member comprises hook and loop material.

13. A method of using an orthopedic ankle orthosis, comprising:
    placing an orthopedic ankle orthosis over a patient's ankle, wherein said orthopedic ankle orthosis comprises a body member and a closure unit, said closure unit comprising a fastener member, a first connector member having a first series of channels, a second connector member having a second series of channels and a pull member;
    pulling the fastener member upwardly with respect to the patient's ankle and thereby tensioning the first connector member downwardly with respect to the ankle and tensioning the second connector member upwardly with respect to the ankle such that a compression force is applied to the patient's ankle from points above and below the ankle only by the first and second connector members; and
    securing the first connector member and second connector member in proximity to one another by removably attaching the fastener member to the body member.

14. The method of claim 13, wherein the first connector member is attached to the orthopedic ankle orthosis at a first position at or above the patient's ankle and the second connector member is attached to the orthopedic ankle orthosis at a second position at or below the patient's ankle.

15. The method of claim 13, wherein pulling the fastener member tightens a pull member interwoven through channels in the first connector member and second connector member.

16. The method of claim 15, wherein the channels comprise a first series of channels in the first connector member and a second series of channels in the second connector member.

17. The method of claim 13, wherein the fastener member is removably attached to the body member by a hook and loop fastener.

18. The method of claim 13, further comprising securing the body member to the patient's ankle by lacing.

19. The method of claim 13, further comprising securing the body member to the patient's ankle with a strap around the patient's lower leg.

20. The method of claim 13, wherein the second connector member is attached to the orthopedic ankle orthosis at a portion configured to cover the sole of a foot.

* * * * *